US00PP10570P

United States Patent [19]

Holtkamp, Sr.

[11] Patent Number: Plant 10,570

[45] Date of Patent: Aug. 25, 1998

[54] AFRICAN VIOLET PLANT NAMED 'PARIS'

[75] Inventor: Reinhold Holtkamp, Sr., Rees-Haffen, Germany

[73] Assignee: International Plant Breeding AG, Bern, Switzerland

[21] Appl. No.: 798,303

[22] Filed: Feb. 7, 1997

[51] Int. Cl.[6] ..... A01H 5/00

[52] U.S. Cl. ..... Plt./69.2

[58] Field of Search ..... Plt./69.2, 69.1

[56] References Cited

U.S. PATENT DOCUMENTS

P.P. 8,136 2/1993 Holtkamp, Sr. ..... Plt./69.2

*Primary Examiner*—James R. Feyrer

*Assistant Examiner*—Kent L. Bell

*Attorney, Agent, or Firm*—Foley & Lardner

[57] ABSTRACT

A new and distinct cultivar of African violet named 'Paris', as described and illustrated, and particularly characterized by its extra large growth habit (35–45 cm in diameter); star-shaped, double, purple flowers with fine white frilled edges; strong stems which curve toward the center to form a bouquet above the leaves; profuse flowering; large, dark green, heart to spear-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha*, and hereinafter referred to by the cultivar name 'Paris'.

The new cultivar was referred to during the breeding and selection process by the designation 906 and is a product of a planned breeding program. The cultivar was originated from a cross made by me in the controlled breeding program in Haffen, Federal Republic of Germany. The female, or seed parent, was a cultivar designated M/72 The male, or pollen parent, was a cultivar designated H 77/906. 'Paris' was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

'Paris' has not been observed under all possible environmental conditions. The phenotype may vary significantly with variations in environment such as temperature, light intensity and day length. The following observations, measurements and values describe the new cultivar as grown in a 15 cm pot in Haffen, West Germany and Nashville, Tenn. under greenhouse conditions which closely approximate those generally used in commercial practice.

The following traits have been repeatedly observed and are determined to be basic characteristics of 'Paris', which in combination distinguish this African violet as a new and distinct cultivar:

(1) 'Paris' will grow as large as 35–45 cm in diameter.

(2) Star-shaped, double, purple flowers with fine white frilled edges.

(3) Strong, wirelike and upright flower stems curving toward the center.

(4) First flash of flowers forms a bouquet above the leaves.

(5) Profuse flowering.

(6) Each plant carries 9–11 and more upright flower stems each of which carries 7–9 and more flowers.

(7) Long lasting, non-dropping flowers.

(8) Plant saleable 10–11 weeks after planting of unrooted shoot.

(9) Seed capsules push slightly through.

(10) Dark green, heart to spear-shaped leaves.

(11) After maturity the flowers dry off, and remain on the peduncle without becoming infected by botrytis.

The accompanying color photographic drawing shows a typical specimen plant of the new cultivar grown in a 15 cm pot. The colors appearing in the photograph are as trite as possible with color illustrations of this type.

In the following description, color references are made to The Royal Horticultural Society Color Chart (RHS), except where general colors of ordinary significance are referred to. Color values were taken under natural sunlight conditions at approximately 12 p.m. in Nashville, Tenn.

Botanical classification: *Saintpaulia ionantha*, Ramat., c.v. 'Paris'.

Parentage:

*Male parent.*—H 77/906.

*Female parent.*—M/72.

*Propagation:* The new cultivar holds its distinguishing characteristics through successive propagations by leaf cuttings.

Plant: From 10 cm to 13 cm tall when grown in pots, and 35–45 cm in diameter when fully grown.

*Leaves.*—General form: Heart to spear-shaped. Diameter: 65–75 mm wide and 80–90 mm long. Texture: Velvety.

Aspect: Hairy, shiny, slightly serrated. Veins: Upperside: visible; underside: well pronounced, light green, shiny. Color (upperside): Yellow-Green Group 147 A and darker. Color (underside): Greyed-Purple Group 186 B. Petiole: Strong, purplish brown, hairy.

*Flowers.*—Buds: Bell-shaped, 7–8 mm just before opening, light green with purplish touch. Sepals: Five (5). Color: Purplish brown. Calyx: Shape: Funnel-shaped. Aspect: Spear-shaped, hairy. Peduncle: Character: Strong upright, hairy. Color: Purplish brown.

*Individual flowers:*—Size: 45–50 mm. Shape: Star-shaped, double. Color (upperside): Between Purple-Violet Group 82 A and Violet Group 87 A and somewhat darker. Under cooler temperatures and more intensive lighting, the purple tends to intensify. Color (underside): Purple-Violet Group 82 B. Borne: Each flower stem carries 7–9 and more flowers on strong, upright peduncles that are free standing above the leaves, thereby forming a bouquet. Flowering habit: Flowers 10–11 weeks after planting an unrooted plantlet.

*Reproductive Organs.*—Stamens: Five (5). Anthers: 5 composed of 10 anther cells, seed capsule pushes slightly through. Filaments: Yellowish green with purplish touch, 4–5 mm long. Styles: 8–9 mm long, purple, base of ovary light green and hairy.

*Roots.*—Normally developed, white when young, turning slightly brownish when older.

Disease resistance: Up to date, 'Paris' has shown very good resistance to all major violet diseases.

GENERAL OBSERVATIONS

'Paris' is an attractive cultivar due to its star-shaped, double, purple flowers with fine white frilled edges. It has an extra large growth habit and is designed to be grown in a 15 cm pot (instead of the regular 10 cm pot). It can reach a diameter of 35–45 cm. (The diameter can vary depending on how firmly the potting medium is compressed). A nice bouquet of flowers free standing above the leaves develops 10–11 weeks after planting an unrooted plantlet. Each of the 9–11 and more strong flower stems carries 7–9 and more flowers which are long-lasting and non-dropping. The bouquet is surrounded by large, dark green, heart to spear-shaped, slightly serrated leaves.

I claim:

1. A new and distinct cultivar of African violet plant named 'Paris', as described and illustrated, and particularly characterized by its extra large growth habit (35–45 cm in diameter); star-shaped, double, purple flowers with fine white frilled edges; strong stems which curve toward the center to form a bouquet above the leaves; profuse flowering; large, dark green, heart to spear-shaped leaves; flowering 10–11 weeks after planting of unrooted shoot, and by its long lasting and non-dropping flowers.

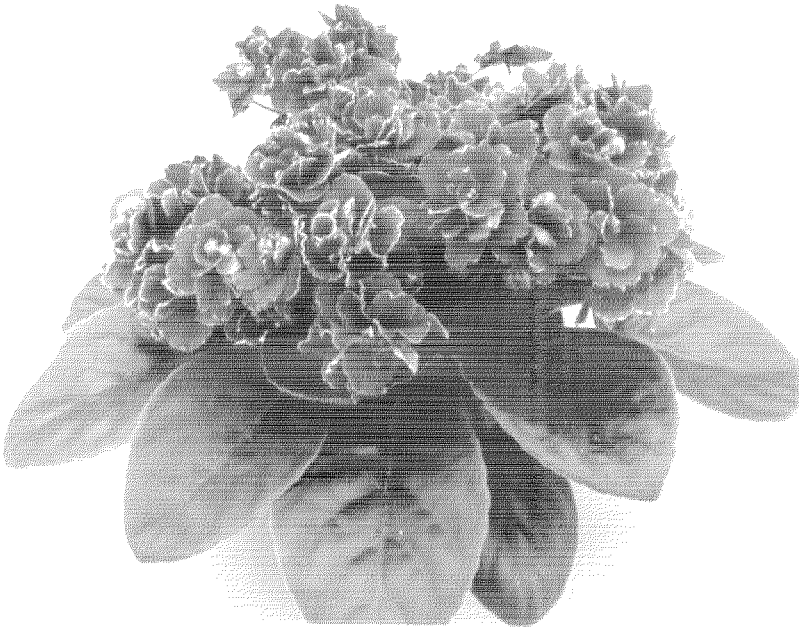

* * * * *